United States Patent [19]

Gupta et al.

[11] Patent Number: 5,559,334
[45] Date of Patent: Sep. 24, 1996

[54] EPIPOLAR RECONSTRUCTION OF 3D STRUCTURES

[75] Inventors: Rajiv Gupta; Richard I. Hartley, both of Schenectady, N.Y.

[73] Assignee: General Electric Company, Schenectady, N.Y.

[21] Appl. No.: 447,021

[22] Filed: May 22, 1995

[51] Int. Cl.⁶ .................................................. G01N 23/02
[52] U.S. Cl. ................................... 250/360.1; 250/358.1
[58] Field of Search ........................... 250/358.1, 359.1, 250/360.1; 378/62, 901

[56] References Cited

U.S. PATENT DOCUMENTS 4,747,574  5/1988  Hofmann ................................ 250/234

OTHER PUBLICATIONS

"Camera Calibration for 2.5 D X-Ray Metrology" by R. Gupta, J. A. Noble, R. I. Hartley, A. M. Schmitz to be Published at the International Conference on Image Processing, to be Held Oct. 22-25, 1995 in Washington, D.C.
"Linear Pushbroom Cameras" by R. I. Hartley, R. Gupta, Presented at the Third European Conference on Computer Vision, Stockholm. Sweden, Computer Vision—ECCV '94, pp. 555-566.
"X-Ray Metrology for Quality Assurance" by J. A. Noble, R. I. Hartley, J. L. Mundy, J. Farley Presented at the 1994 International Conference on Robotics and Automation, Proc. IEEE International Conference on Robotics and Automation, pp. 1113-1119, San Diego, CA. May 8-13, 1995.
"Cad-Based Inspection Using X-Ray Stereo" by J. A. Noble, R. Gupta, J. L. Mundy, R. I. Hartley, W. Hoffman Presentation to ICRA '95 Nagota, Japan, May 21-27, 1995.

*Primary Examiner*—David P. Porta
*Assistant Examiner*—David Vernon Bruce
*Attorney, Agent, or Firm*—Lawrence P. Zale; Marvin Snyder

[57] ABSTRACT

A method of reconstructing selected features of a part manufactured according to a CAD model involves acquiring a set of linear push broom (LPB) projection images of the part acquired at different angles about an axis of rotation passing through the part. Acquiring a set of matrices $M_j$ j=1 . . . N, each of which maps 3D coordinates of the part to screen coordinates of one of the projection images. Reconstruction of 3D structures from the projection images requires identification of screen coordinates of each image which correspond to a point of the structure of the part to be reconstructed. Back projecting these screen coordinates modified by the distortion inherent in the LPB imaging device. This is accomplished by selecting a screen coordinate on a feature desired to be reconstructed. Computing a ray passing through the selected screen coordinate through an imaging center. Using each M matrix to map this ray to a hyperbola on the other images. The hyperbola is then scanned until the desired feature is encountered. This second screen location of this projection image corresponds to the first selected screen location. A second ray through the second screen coordinate is constructed. Where it intersects the first ray identifies the 3D reconstruction point. This is repeated for a number of points to create a reconstruction of the selected feature.

2 Claims, 2 Drawing Sheets

EPIPOLAR RECONSTRUCTION OF 3D STRUCTURES

CROSS REFERENCE TO RELATED APPLICATIONS

This application is related to U.S. patent application "Method Of Calibration Of Imaging Devices" by R. Gupta, J. Noble, R. Hartley, A. Schmitz (Atty. Docket No. RD-24, 108) filed concurrently with this application, incorporated by reference and assigned to the present assignee.

BACKGROUND OF THE INVENTION

1. Field of the Invention

This invention pertains to non-destructive testing of manufactured parts and more specifically, use of projection imaging in non-destructive testing.

2. Description of Related Art

In the manufacturing of parts, an engineer creates a design or blueprint of locations and shapes of structures of the part identified in part coordinate system. These may be designed on a CAD/CAM workstation. Machines manufacture the part according to the design, or CAD model, but mechanical error causes differences between the manufactured part and the theoretical design (CAD model). In order to insure proper quality, the manufactured parts are examined, typically by non-destructive testing to insure accurate construction. Those which fail are either re-manufactured or discarded.

A typical type of non-destructive testing involves imaging of the part such that internal structures are visible. One such type of imaging is X-ray imaging, employing an X-ray imaging device which creates 2D projection images of the 3-D part. This usually requires calibration of the imaging device.

Geometric calibration of an imaging device refers to the ability to map the 3-D world to an image plane of the image device. If the geometric calibration of a imaging device is known, one can locate in the image any arbitrary point in space.

Two methods for geometrically calibrating an imaging device, and in general, any imaging setup, are prevalent in non-destructive testing.

In the first method, one explicitly measures the various parameters that determine the mapping from the 3-D world to the 2-D image plane. For example, the focal length, the distance from the source to the center of the part, the source to detector array distance, the detector spacing, the spacing between image lines, etc. are measured. Knowing these parameters, any point of the object space can be projected into the image. This method will be referred to as the "direct calibration".

Direct calibration suffers from the following disadvantages.

1. The calibration is done once and frozen till the next calibration run, so it does not reflect any changes in imaging parameters from one image acquisition to the next. One has to do direct calibration often enough in order to minimize the effects of changes in the calibrated parameters between acquisitions.

2. In many manufacturing situations, in-situ calibration is essential because the setup is not repeatable. In these cases direct calibration cannot be used.

3. The measured parameters may fluctuate from image to image.

In another calibration method, specially designed, precisely calibrated parts or patterns are imaged to either deduce the imaging parameters or to adjust the imaging device to a known calibration. For example, one might image a pattern of parallel wires with decreasing spacing to determine the magnification and the resolution of the imager. This calibration method also suffers from all three disadvantages mentioned above.

Typically, a part is examined by placing it in a fixture, known as a 'six point nest', having reference structures located at specific known points on the fixture. The distance from each of 6 preselected points on the surface of the part to the reference structures is determined. These distances are compared to preset tolerance distances to determine if the part is to be rejected.

The use of a six-point nest to orient a part to be examined is commonplace. Sometimes, the part is machined, while in its six-point nest, to provide alternate places to hold the part while retaining the same location relative to the fixture.

In order to deduce the orientation of the part in an X-ray image, locations of the fixture and visible features on the part are essential.

Another method of non-destructive testing compared the CAD model with a 3D model constructed from a number of projection images.

Reconstruction Method

The current state of the art requires a complete volumetric reconstruction of the part which is then compared to the CAD model. The part is rotated and imaged in the field of view of an imaging device, at successive angular positions covering a full range of 360 degrees. These images can be then assembled into a complete volumetric 3D model of the part using techniques borrowed from computed tomography (CT).

Volumetric CT approaches for part geometry reconstruction/validation suffer from the following disadvantages.

1. Even if only a few key features of the part are of interest, all images covering the full angular range must be acquired.

2. The complete volume, or at least several complete cross-sectional slices must be reconstructed and typically does not allow volume-of-interest reconstruction.

3. Because of the inherent complexity of the reconstruction algorithm, these techniques tend to be computationally intensive and take a long time to reconstruct the volume. Typically, they require powerful processors and unique hardware to speed-up the computation.

4. Since the complete volume is always reconstructed, the desired information (e.g., how far is a given feature from its nominal location) has to be derived from the 3-D volume. This typically entails segmentation of the 3-D volume, then identification of the desired structure in the segmented volume.

SUMMARY OF THE INVENTION

A method of reconstructing structures of a part from a number of linear pushbroom (LPB) projection images when the calibration matrices $M_j$ employs acquiring the projection images at different angles about an axis of rotation passing through the part. Selecting a point on a structure desired to be reconstructed having screen coordinates $(u_1,v_1)$ and a pixel intensity I.

Creating a first ray passing through the selected screen coordinate and through a center of projection.

Multiplying a plurality of points along the ray by the matrix $M_j$ to result in screen coordinates being approximately a hyperbola on a second projection image.

Correlating intensities along the hyperbola to the intensity I to determine a second set of screen coordinates $(u_2,v_2)$ on the second projection image indicating where the hyperbola intersects the selected structure. The second set of screen coordinates corresponding to the same point of the part as does the first set of screen coordinates $(u_1,v_1)$. Creating a second ray passing through the second set of screen coordinates $(u_2,v_2)$ and through a center of projection. Identifying a 3D location where the rays intersect as the reconstructed point repeating these steps the points on the desired structure. And finally displaying the 3D reconstructed point to result in a reconstructed 3D structure.

OBJECT OF THE INVENTION

An object of the present invention is to identify screen image points of two or more linear push broom projection images which trace back to the same common object point of an object being imaged.

Another object of the present invention is to reconstruct selected features of a part imaged with linear pushbroom projection images.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawing in which:

DETAILED DESCRIPTION OF THE INVENTION

Figure 1:
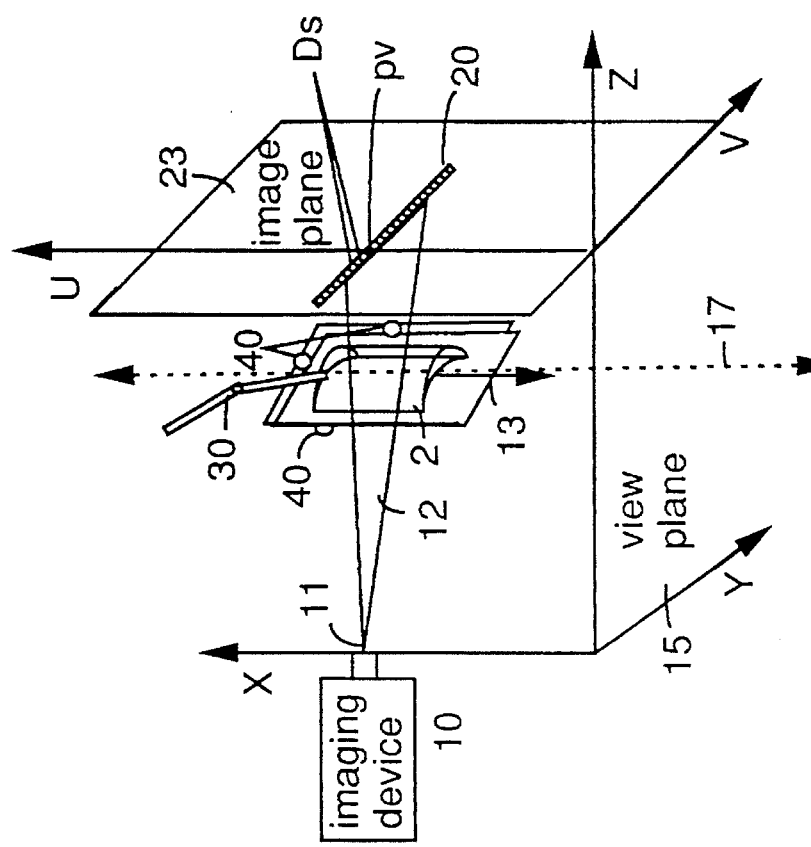
FIG. 1 a partial block diagram and perspective view of the part being imaged and illustrates the projection image geometry and relative position of the coordinate systems.

In FIG. 1, a common setup for non-destructive testing an object to be inspected is positioned between a imaging device 10 capable of imaging internal structures of the object, which may be a point X-ray source, or other point radiation source; and a detector 20 shown here as a linear array of detector elements having a spacing Ds. An actuating device 30, such as a mechanical robot arm, moves object 2 along a line of motion 13 perpendicular to a fan beam 12 from imaging device 10. A 2-D image of object 2, consisting of several 1-D projections, is collected. Each image collected in this manner is orthographic in the direction of line of motion 13 and perspective in the orthogonal direction. These ortho-perspective images of object 2 are traditionally used for non-destructive testing. This scanning arrangement shall be referred to as a linear pushbroom (LPB) imaging device.

Besides moving object 2, typically actuating device 30 can also rotate it through any desired angle with line of motion 13 as the axis of rotation. This allows imaging of object 2 in different orientations.

In FIG. 1, 3-D points of part 2 are mapped to 2-D image points by the imaging device 10. Axes U and V are oriented as shown in an image plane 23. An imager coordinate system is employed which is fixed with respect to imaging device 10. The origin of the imager coordinate system is an imaging point source 11, or the center of projection. The Y axis lies in a view plane 15 parallel to linear sensor array 20. The Z axis lies perpendicular to the Y axis and directed so that the visible points have positive Z coordinates. The X axis is oriented to view plane 15 such that X, Y and Z axes form right-handed coordinate system. The Y axis is oriented such that successive image lines have a lower X value.

During a scan, object 2 moves along line of motion 13 at a constant velocity with respect to view plane 15. The orientation of view plane 15 is constant with respect to the line of motion.

Because of the asymmetry in how screen locations (u,v) are extracted, a linear pushbroom (LPB) image may be thought of as a projective image in one direction (the V direction) and an orthographic image in the other direction (the U direction).

Imaging device calibration refers to the task of determining conversion of the 3D locations of object 2 to 2D screen locations of the projection images. The present invention includes a method for geometrically calibrating various projections produced by a LPB setup.

In LPB geometry, image device 10 maps 3D locations $(x',y',z')$ of part 2 to 2-D image coordinates $(u,v)$ given by:

$$\left\{ \begin{array}{c} u \\ wv \\ w \end{array} \right\} = \left\{ \begin{array}{ccc} 1 & 0 & 0 \\ 0 & f/D_s & p_v \\ 0 & 0 & 1 \end{array} \right\} \left\{ \begin{array}{ccc} 1/D_x & 0 & 0 \\ -D_y/D_x & 1 & 0 \\ -D_z/D_x & 0 & 1 \end{array} \right\} \left\{ \begin{array}{c} x' \\ y' \\ z' \end{array} \right\} \quad (1)$$

where f is the focal length (or magnification) of imaging device 10, Ds is the spacing between adjacent detector elements of detector 20, pv is a principal point offset in the v direction, being the v screen coordinate of a perpendicular through imaging device 10 and detector 20, and $(D_x, D_y, D_z)$ is the displacement vector (i.e., robot arm 30 motion) from one image row to the next.

In a given acquisition run, robot arm 30 moves part 2 to be scanned through the line of motion 13 to acquire a projection image. Robot arm 30 then rotates part 2 and scans it again to create another projection image. Thus, each projection image in an acquisition run corresponds to a different translation and rotation vector. $R_j$ is a rotation matrix for robot arm 30 when the jth image was acquired, and $T_j$ is the translation vector for robot arm 30 at the start of the jth scan. The transformation from 3D imager coordinate system to the screen coordinate system is given by:

$$\left\{ \begin{array}{c} u_j \\ w_j v_j \\ w_j \end{array} \right\} = \quad (2)$$

-continued $$\left\{\begin{matrix} 1 & 0 & 0 \\ 0 & f/D_s & p_v \\ 0 & 0 & 1 \end{matrix}\right\} \left\{\begin{matrix} 1/D_x & 0 & 0 \\ -D_y/D_x & 1 & 0 \\ -D_z/D_x & 0 & 1 \end{matrix}\right\} (R_j^i - R_j T_j) \left\{\begin{matrix} x' \\ y' \\ z' \\ 1 \end{matrix}\right\}$$

This may be denoted as:

$$\left\{\begin{matrix} u_j \\ w_j v_j \\ w_j \end{matrix}\right\} = M_j \left\{\begin{matrix} x' \\ y' \\ z' \end{matrix}\right\} \quad (3)$$

For a more detailed discussion of LPB imaging device refer to "Linear Pushbroom Cameras" by Richard Hartley, Rajiv Gupta presented at the Third European Conference on Computer Vision, Stockholm, Sweden, "Computer Vision—ECCV '94, which is hereby incorporated by reference.

Typically object 2 is machined or molded using a CAD model as the plan. Since all geometric information about object 2 is specified according to a CAD coordinate system, it is useful to define a relationship not only between the screen coordinates of the projection images and part 2 defined in imager coordinate system; but between screen coordinates of the projection images, imager coordinates of part 2, and CAD coordinates.

Figure 2:
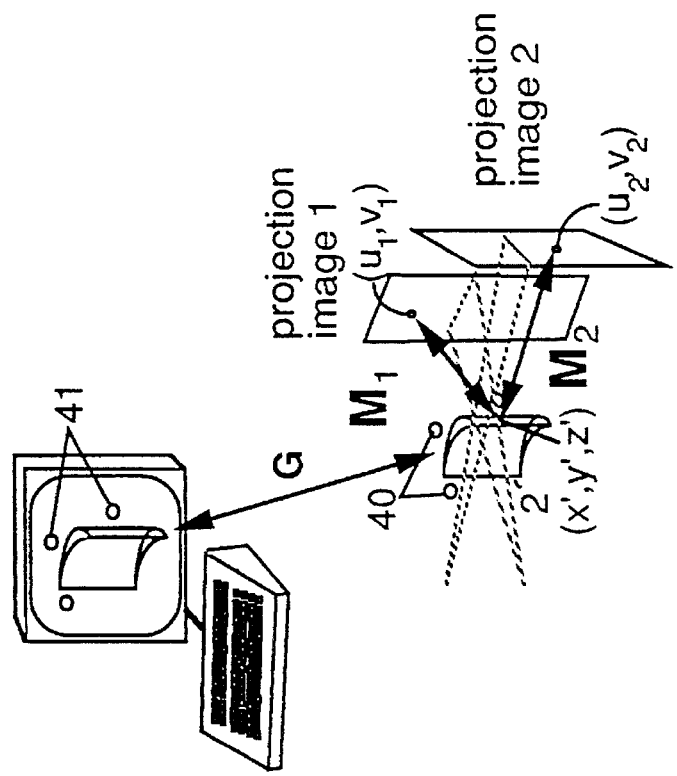
FIG. 2 is a block diagram illustrating the transformation matrices between a CAD model coordinate system an imaging device coordinate system and a screen coordinate system.

However, there is still is another transformation which must be determined, that being the transformation of the CAD coordinate system to the imager coordinate system. This may be described by an angular rotation between the X axes θ, an angular rotation between the Y axes being φ, and an angular rotation between the Z axes being κ of the two coordinate systems; and a translation from the origin of the CAD coordinate system to the origin of the imager coordinate system. This matrix, which is a standard (3×4) solid body rotation/translation coordinate transformation matrix, will be known as global matrix G. G does not change from image to image but merely defines a 3-D axis rotation and translation between the CAD and imager coordinate systems as shown in FIG. 2. The matrices, however, $M_1, M_2, M_3 \ldots M_N$, where N is the number of angular projection images taken, differs from image to image.

The coordinate transformation between the CAD coordinate system and the imager coordinate system may be grouped into a single global matrix G. By grouping, and utilizing Eq. (2), Eq. (3) reduces to:

$$\left\{\begin{matrix} u_j \\ w_j v_j \\ w_j \end{matrix}\right\} = M_j \cdot G \cdot \left\{\begin{matrix} x \\ y \\ z \\ 1 \end{matrix}\right\}. \quad (4)$$

One of the main goals of the present invention is to relate locations of the CAD model to those of the projection images, as shown in FIG. 2. In the CAD model, there are markers 41 centered in several selected known points. These are positioned at exact points (x, y, z) known in the CAD model coordinate system for each of the markers.

Physical markers 40, which may be "tooling balls" of FIGS. 1, 2, are selected of a material which show up opaque on the projection images. These are fixed to a fixture at very accurate positions. Also, the position of each of these tooling balls relative to the others is a very accurate representation of that in the CAD model. When part 2 is positioned on the fixture having the tooling balls 40, the location of part 2 can be adjusted such that the tooling balls are a fixed distance from points of the part known with accuracy. Typically, in machining, a part is not rejected if several locations on its surface points are correct within a predetermined tolerance. These are measured during quality control. The fixture takes this into account and positions part 2 such that one of the points on its surface known to be accurate is a known distance from the tooling balls. This allows part 2 to be positioned relative to the tooling balls just as the CAD model of part 2 is positioned to its tooling balls.

Images are taken by imaging device 10 of part 2 at several different angles about an axis of rotation 17 passing through part 2. All other parameters of imaging device 10 are not adjusted. As mentioned above, it is important to relate desired points of an image to points on the CAD model.

A matrix transformation $M_1$ which would convert points of part 2 (x',y',z') to a screen location $(u_1,v_1,)$ is desired. Similarly, a transformation matrix $M_2$ is desired which would map the same location of object 2 (x',y',z') to a screen location on image 2 $(u_2, v_2)$.

If one can determine accurately the transformation matrix G, and the transformation matrices $M_1, M_2, M_3 \ldots M_N$, one would be able to accurately determine where each point of the CAD model (x,y,z) would appear in each of the projection images.

Knowing beforehand that the CAD model has locations which are a specified distance from each of the physical markers 40, and that the physical part 2 has been fixed on a fixture 19 such that known points of object 2 are the same distance from physical markers 40 as would be in the CAD model, it is possible to determine G and the M matrices.

Defining $u_{ij}$ as the unscaled screen coordinates for the ith point and the jth image, being a vector $$\left\{\begin{matrix} u_{ij} \\ w_{ij} v_{ij} \\ w_{ij} \end{matrix}\right\}$$

where $w_{ij}$ is an unknown scale factor, and $(u_{ij}, v_{ij})^T$ are the actual screen coordinates. $x_i$ is the ith point in the CAD model corresponding to the screen coordinates $u_{ij}$, the equation converting CAD points to screen locations would be:

$$u_{ij} = M_j G x_i \text{ for } i=1, 2, 3, \ldots n; j=1, 2, 3 \ldots N, \quad (5)$$

where n is the number of points and N is the number of projection images.

Since the locations in the CAD model of the CAD markers are known, and the screen locations of the physical markers on the projection images is known for each image, plugging these into Eq. (5) would allow an estimation of the global matrix G, and matrices $M_j$.

Them are iterative methods of solving for these matrices as described above but the process may be more accurate by recognizing a few details and making a few assumptions. First of all, many of the intrinsic parameters of imaging device 10 deviate very little from image to image in a single acquisition run. These intrinsic parameters include focal length, f, the detector element spacing $D_s$ of detector array 20, the principal point offset $p_v$ of the detector array with relation to the point source. Also, the vector (Dx, Dy, Dz) indicating the displacement of part 2 as an individual scan line is acquired is fairly constant from one projection image to the next.

Therefore, focal length $f_1$ for the first projection image of matrix $M_1$ would constrained to be equal to the focal length $f_2$ of matrix $M_2$, and focal length $f_3$ of matrix $M_3$ etc. up until focal length $f_N$ of matrix $M_N$. In general, the various $M_j$ matrices differ only by a rotation around a common axis, the axis or rotation of imaging device 10. By employing these additional constraints, the number of unknowns is significantly reduced while retaining the same number of equations. The accuracy of the iteration is directly related to the number of unknowns to the number of equations.

Some iteration methods also require a starting point being somewhat "in the ball park" of the actual expected numbers to reduce the effects of falling into "local minima". Therefore, the procedure begins by first selecting approximate values for elements of the M matrices. These may be known from other means. For instance a value of f=2 meters may be measured by some other experiment and used as an approximate value of the focal length. The 3-D CAD locations of the tooling balls along with their corresponding 2-D screen locations are then employed to iteratively determine an approximate initial value for the matrix G.

This initial value of global matrix G is then employed in a second step of iteration again using the CAD locations of the tooling balls and the corresponding screen locations of the tooling balls in the projection images, but now both the M matrices, and the G matrix are allowed to vary. This further refine the estimate of matrix G and the M matrices.

The resultant M matrices are used to create a 3D structure from a collection of related 2D screen coordinates. The G matrix maps the 3D CAD model to the 3D part, or 3D reconstructed part structure. Now it is possible to do a point to point mapping. This may become very tedious without an automated method of 3D reconstruction.

Accuracy Estimation

This method was performed on physical part 2. The results of accuracy estimation are presented here. Five tooling balls on a fixture were used to refine imaging parameters as well as estimate the 3-D to 3-D global transformation. To judge the prediction accuracy, the models were first computed using a set of four balls. These models were then used to predict the location of the fifth tooling ball in 3-D. Each ball was made the "unknown ball" in turn and the error in its prediction was computed. The results for 4 projection images taken 90 degrees apart are shown below:

| Ball | Actual Location | Computed Location | Error |
|---|---|---|---|
| 1 | (−1.13, −1.5, −0.456) | (−1.1312344, −1.4956774, −0.4556899) | 0.0045060 |
| 2 | (0.37, −1.5, 0) | (0.3723350, −1.5039249, −0.0015843) | 0.0048340 |
| 3 | (−0.13, −0.393, 1) | (−0.1282013, −0.3891031, 1.0003347) | 0.0043050 |
| 4 | (0.37, 0.5, 0) | (0.3642777, 0.5004171, 0.0005916) | 0.0057679 |
| 5 | (−0.13, −0.393, 1) | (−0.1266846, −0.3940490, −0.9998815) | 0.0034795 |

Accuracy of parameter refinement with 4 Views with a total angular span of 90 degrees.

All errors are less than 6 mils and the average error is about 4.6 mils. There is about a 3-fold increase in accuracy with the calibration refinement, both in worst and average errors, over what is known as 'ideal calibration'.

Accuracy can be further improved by increasing the angular separation of the views. For example, if five views with an angular separation of 120 degrees are used, all errors are less than 3.5 mils and the average error is about 2.5 mils.

| Ball | Actual Location | Computed Location | Error |
|---|---|---|---|
| 1 | (−1.13, −1.5, −0.456) | (−1.1317865, −1.4993739, −0.4543137) | 0.0025352 |
| 2 | (0.37, −1.5, 0) | (0.3713346, −1.5012003, −0.0000732) | 0.0017965 |
| 3 | (−0.13, −0.393, 1) | (−0.1297478, −0.3909793, 0.9989194) | 0.0023054 |
| 4 | (0.37, 0.5, 0) | (0.3674070, 0.4979143, 0.0010658) | 0.0034943 |
| 5 | (−0.13, −0.393, −1) | (−0.1282856, −0.3918528, −1.0012742) | 0.0024246 |

A Method for Selective 3-D Reconstruction

A new method for 3-D reconstruction of desired structures of object 2 requires only a limited number of projection images. Also only those portions of object 2 that are desired may be selectively reconstructed without the need to reconstruct an entire model or slice.

2-D features in multiple projection images acquired at different angles are delineated, and then this information is assembled into a partial 3-D model using pre-computed calibration matrices G, and the $M_j$ matrices computed earlier. Thus, there are two main steps in the 3-D feature reconstruction method: (1) identification of the 2-D screen coordinates pertaining to a desired feature on each projection image, and (2) 3-D feature reconstruction from the 2D screen coordinates.

2-D Feature Extraction

The user employs a mouse or other pointing device to select a structure, or feature, of each image displayed on a monitor. Alternately, a user may select a region encompassing the feature. Conventional image segmentation technique can be used for identifying the screen coordinates pertaining to the selected 2-D feature. These techniques include, but are not limited to, adaptive or non-adaptive thresholding, snakes, deformable templates, all types of edge detectors, region growing techniques, and similar conventional techniques. At the end of this procedure, the feature to be reconstructed is clearly demarcated as a collection of 2-D screen coordinates in each projection image.

3D Feature Reconstruction

The selected screen coordinates for the selected feature are used to reconstruct a 3D model.

Figure 3:
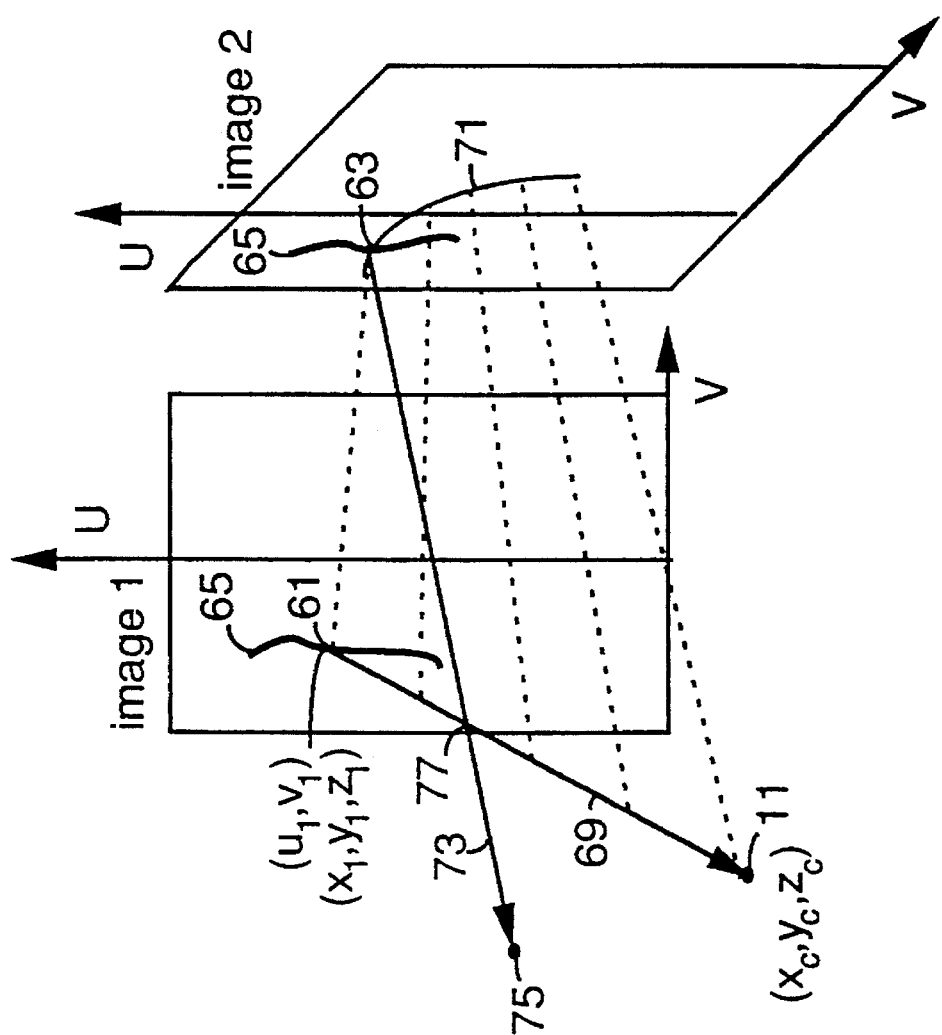
FIG. 3 is a graph illustrating the mapping of a ray to a hyperbola used in determining corresponding points in several projection images.

Reconstruction of 3D structures from the projection images requires identification of corresponding screen coordinates between images for a given point of the selected structure or feature 65, as shown in FIG. 3. This may be difficult for points which are not end points of a structure. Take, for example, a hole drilled in a part. The end point of the hole in each of the images may be discernible. Each top endpoint corresponds to the top end point in each of the images, and the bottom end point similarly, corresponds to the bottom end point of each image. Where it gets difficult is determining a screen locations of other images corresponding to a screen coordinate somewhere within the hole selected on a first image.

Correspondence between screen locations across projection images is accomplished by 'epipolar matching'. This requires selecting a screen location 61 on a projection image 1 of a feature 65 desired to be reconstructed. Next a ray 69 is computed passing through the selected screen location 61 through the center of projection 11 according to:

$$\left\{\begin{array}{c} u_i \\ w_i v_i \\ w_i \end{array}\right\} = M_i \left\{\begin{array}{c} x \\ y \\ z \\ 1 \end{array}\right\} \quad (6a)$$

This gives an equation of the form:

$$line = V_p + tV_a, \quad (6b)$$

where $V_p$ is a point on the line, being either the selected screen location 61 or the center of projection 11, t is a parametric 'dummy variable', and $V_a$ is a vector along the direction of the line. Constraining the reconstructed location (x,y,z) to be on the line results in:

$$(x,y,z) = V_p + tV_a. \quad (7)$$

Employing Eqs. (2) and (7), the mapping of ray 69 onto projection image 2 is defined by:

$$u_j = m_{1j}^T (V_p + tV_a) \quad (8)$$

$$v_j = \frac{m_{2j}^T (V_p + tV_a)}{m_{3j}^T (V_p + tV_a)}$$

where $m_{ij}^T$ is the ith row of calibration matrix $M_j$.

This maps ray 69 to a hyperbola 71 of projection image 2.

If the screen location 61 of a projection image 1 pertains to a 3D point $(x_1, y_1, z_1)$, and the center of projection 11 pertains to a 3D point $(x_c, y_c, z_c)$, then the equation for ray 69 will be $$(x,y,z) = (x_1, y_1, z_1) + t(x_c - x_1, y_c - y_1, z_c - z_1) \quad (9)$$

Ray 69 is then mapped on the other projection images as described above for other projection images using the calibration matrices M corresponding to each projection image.

Each point along hyperbola 71 is tested to determine if it pertains to selected feature 65. This may be performed visually, or by computer assisted techniques such as, adaptive or non-adaptive thresholding, snakes, deformable templates, all types of edge detectors, region growing techniques, and similar conventional techniques. When feature 65 is encountered, a second screen location 63 is noted. Second screen location 63 of projection image 2 corresponds to screen location 61 of projection image 2, such that both are images of a common point of part 2.

A second ray 73 passing through second screen coordinate 63 and the imaging center 75 for this projection image, is constructed. Second ray 73 intersects first ray 69 at a 3D reconstruction point 77.

This process is repeated for a number of screen locations pertaining to feature 65 to create a 3D reconstruction of feature 65.

The present invention may be employed in comparing structures of part 2 with its CAD model.

Desired Structure Reconstruction

The present invention was employed to reconstruct holes drilled in a part. In the ideal case, a 3-D hole location can be represented by a cylinder which projects to rectangular feature in a 2-D projection image. (As stated above, cylindrical holes drilled in object 2 are described, but other structures may also be used.)

In this case, the simplest form of reconstruction algorithm assumes that the end points of the hole can be precisely located (manually or automatically) in a number of images. Using the calibration matrix M for each view, the 3-D locations of points other than the end points can then be computed directly by solving a set of equations that minimize the overall RMS reproduction error in all views.

In many instances, however, it is difficult to discern the end-points of a hole because of its orientation with respect to the detector array, the thickness of the part in its neighborhood and/or the orientation of object surfaces with respect to its axis. The hole may also have a tapered end if it is drilled obliquely to the surface of the part. A more reliable measure to compute is the orientation of the hole. As a result, a line-based reconstruction method is more effective. In this approach, linear features, such as the axis of the hole, are extracted in each projection image.

Epipolar curve matching is performed to establish image-to-image points, and triangulation used for 3-D reconstruction. This approach is more accurate and robust than a point-based reconstruction method. For a more detailed description of this, and other topics, and experimental results, please refer to "2.5 D X-Ray Metrology" by Rajiv Gupta, J. Alison Noble, Richard Hartley, Joe Mundy, Andrea Schmitz to be published at the International Conference on Image Processing, to be held Oct. 22–25, 1995 in Washington, D.C.; and "X-ray Metrology for Quality Assurance" by J. Alison Noble, Richard Hartley, Joe Mundy, J. Farley presented at the 1994 International Conference on Robotics and Automation, Proc. *IEEE International Conference on Robotics and Automation* pp. 1113–1119, San Diego, Calif. May 8–13; both hereby incorporated by reference.

An overall discussion of these topics is described in "CAD-based Inspection Using X-Ray Stereo" by J. Alison Noble, Rajiv Gupta, Joe Mundy, Richard Hartley, W. Hoffman presentation to 1995 International Conference on Robotics and Automation (ICRA '95) Nagota, Japan May 21–27, 1995" also hereby incorporate by reference.

While several presently preferred embodiments of the invention have been described in detail herein, many modifications and variations will now become apparent to those skilled in the art. It is, therefore, to be understood that the appended claims are intended to cover all such modifications and variations as fall within the true spirit of the invention.

What we claim is:

1. A method of reconstructing structures of a part from N linear pushbroom (LPB) projection images, where N is greater than 1, given the mapping matrices $M_j$ for each of the projection images j=1 . . . N comprising the steps of:

a) acquiring a plurality of linear pushbroom images at different angles about an axis of rotation passing through the part;

b) selecting a first set of screen coordinates $(u_1, v_1)$ having an intensity I of a first projection image being part of a feature desired to be reconstructed;

c) creating a first ray passing through the selected screen coordinate and through a center of projection;

d) multiplying a plurality of points along the ray by the matrix $M_j$ to result in substantially a hyperbola on a second projection image;

e) correlating intensities along the hyperbola to intensity I to determine a second set of screen coordinates $(u_2, v_2)$ on the second projection image where the hyperbola intersects the selected structure, the second set of screen coordinates $(u_2, v_2)$ corresponding to the same point on said part as the first set of screen coordinates $(u_1, v_1)$ f) creating a second ray passing through the second set of screen coordinates $(u_2, v_2)$ and through a center of projection;

g) identifying a 3D location where the rays intersect as the reconstructed point; and h) repeating steps "b"–"g" for a plurality of points on the desired feature; and i) displaying the 3D reconstructed point to result in a reconstructed 3D structure.

2. A method of reconstructing structures of a part from N linear pushbroom (LPB) projection images, where N is greater than 1, given the mapping matrices $M_j$ for each of the projection images $j=1 \ldots N$ comprising the steps of:

a) acquiring a plurality of linear pushbroom images at different angles about an axis of rotation passing through the part;

b) selecting a first set of screen coordinates $(u_1, v_1)$ having an intensity I on an initial projection image, the first set of coordinates being part of a feature desired to be reconstructed;

c) creating a first ray passing through the selected screen coordinate and through a center of projection;

d) multiplying a plurality of points along the ray by the matrix $M_j$ to result in a hyperbola on another projection image j;

e) correlating intensities along the hyperbola to intensity I to determine a jth set of screen coordinates $(u_j, v_j)$ on projection image j where the hyperbola intersects the selected structure, the jth set of screen coordinates $(u_j, v_j)$ corresponding to the same point on said part as the first set of screen coordinates $(u_1, v_1)$;

f) creating a jth ray passing through the jth set of screen coordinates $(u_j, v_j)$ and through a center of projection;

g) repeating steps "d"–"f" for a plurality of projection images;

h) identifying a 3D location where the rays intersect as the reconstructed point; and i) repeating steps "b"–"h" for a plurality of points on the desired feature; and j) displaying the 3D reconstructed point to result in a reconstructed 3D structure.

* * * * *